United States Patent
Mestl et al.

(10) Patent No.: US 11,161,096 B2
(45) Date of Patent: Nov. 2, 2021

(54) SYNTHESIS OF A MOVNBTE CATALYST HAVING AN INCREASED SPECIFIC SURFACE AND HIGHER ACTIVITY FOR THE OXIDATIVE DEHYDROGENATION OF ETHANE TO ETHYLENE

(71) Applicant: Clariant Produkte (Deutschland) GmbH, Frankfurt am Main (DE)

(72) Inventors: Gerhard Mestl, Munich (DE); Klaus Wanninger, Kolbermoor (DE); Daniel Melzer, Munich (DE); Maria Cruz Sanchez-Sanchez, Munich (DE); Julia Tseglakova, Muehlheim an der Ruhr (DE); Johannes Lercher, Ottobrunn (DE)

(73) Assignee: CLARIANT PRODUKTE (DEUTSCHLAND) GMBH, Frankfurt Am Main (DE)

( * ) Notice: Subject to any disclaimer, the term of this patent is extended or adjusted under 35 U.S.C. 154(b) by 40 days.

(21) Appl. No.: 16/480,736

(22) PCT Filed: Jan. 26, 2018

(86) PCT No.: PCT/EP2018/052012
§ 371 (c)(1),
(2) Date: Oct. 3, 2019

(87) PCT Pub. No.: WO2018/141653
PCT Pub. Date: Aug. 9, 2018

(65) Prior Publication Data
US 2020/0139349 A1  May 7, 2020

(30) Foreign Application Priority Data
Jan. 31, 2017 (DE) .......................... 102017000865.5

(51) Int. Cl.
*B01J 23/28* (2006.01)
*B01J 23/00* (2006.01)
(Continued)

(52) U.S. Cl.
CPC ............. *B01J 23/28* (2013.01); *B01J 23/002* (2013.01); *B01J 35/1038* (2013.01);
(Continued)

(58) Field of Classification Search
CPC ...... B01J 23/28; B01J 35/002; B01J 35/1014; B01J 35/1019; B01J 35/1023;
(Continued)

(56) References Cited

U.S. PATENT DOCUMENTS

| 5,281,745 A | 1/1994 | Ushikubo |
|---|---|---|
| 5,380,933 A | 1/1995 | Ushikubo |

(Continued)

FOREIGN PATENT DOCUMENTS

| DE | 10119933 | 10/2002 |
|---|---|---|
| EP | 0318295 | 5/1989 |

(Continued)

OTHER PUBLICATIONS

Melzer, D. et al. (2019) Design and synthesis of highly active MoVTeNb-oxides for ethane oxidative dehydrogenation. Nat Commun 10, 4012 (2019). https://doi.org/10.1038/s41467-019-11940-0.*

(Continued)

*Primary Examiner* — Brian A McCaig

(57) ABSTRACT

A novel mixed oxide material is disclosed which comprises molybdenum, vanadium, tellurium and niobium and the use of the mixed oxide material as catalyst for the oxidative (Continued)

dehydrogenation of ethane to ethene or the oxidation of propane to acrylic acid and a process for producing the mixed oxide material.

7 Claims, 10 Drawing Sheets

(51) Int. Cl.
*B01J 35/10* (2006.01)
*B01J 37/03* (2006.01)
*C07C 5/48* (2006.01)

(52) U.S. Cl.
CPC ....... *B01J 35/1042* (2013.01); *B01J 35/1047* (2013.01); *B01J 37/031* (2013.01); *C07C 5/48* (2013.01); *C07C 2523/20* (2013.01); *C07C 2523/22* (2013.01); *C07C 2523/28* (2013.01); *C07C 2527/057* (2013.01); *Y02P 20/52* (2015.11)

(58) Field of Classification Search
CPC ................ B01J 35/1038; B01J 35/1042; B01J 35/1047; B01J 37/031; B01J 37/033; B01J 37/036; B01J 2523/00; Y02P 20/52; C07C 5/48; C07C 51/252; C07C 2523/20; C07C 2523/22; C07C 2523/28; C07C 2527/057

See application file for complete search history.

(56) References Cited

U.S. PATENT DOCUMENTS

| | | | |
|---|---|---|---|
| 5,929,256 | A | 7/1999 | Felthouse |
| 6,723,869 | B1 | 4/2004 | Mori |
| 6,867,328 | B2 | 3/2005 | Borgmeier |
| 7,009,075 | B2 | 3/2006 | Hazin |
| 7,038,082 | B2 | 5/2006 | Borgmeier |
| 9,073,036 | B2 | 7/2015 | Hagemeyer |
| 9,254,482 | B2 | 2/2016 | Hagemeyer |
| 10,387,233 | B2 | 8/2019 | Kinjo |
| 10,807,073 | B2 | 10/2020 | Tamura |
| 2003/0013904 | A1 † | 1/2003 | Chaturvedi |
| 2005/0027295 | A1 | 2/2005 | Yang |
| 2005/0277546 | A1 | 12/2005 | Hibst |
| 2014/0336411 | A1 | 11/2014 | Hagemeyer |
| 2015/0148563 | A1 † | 5/2015 | Hagemeyer |
| 2016/0030937 | A1 † | 2/2016 | Gabriel |

FOREIGN PATENT DOCUMENTS

| | | |
|---|---|---|
| EP | 1598112 | 11/2005 |
| JP | 07232071 | 9/1995 |
| JP | 07053414 | 9/1996 |
| JP | 08226796 | 9/1996 |
| JP | 2000143244 | 5/2000 |
| WO | 2008068332 | 6/2008 |
| WO | 2009106474 | 9/2009 |

OTHER PUBLICATIONS

Kolen'ko, Y.V. et al (2011) ChemCatChem, 3, 1597-1606.*
Desanto, Peter, Structural aspects of the M1 and M2 phases . . . Z. Kristallogr. 219 (2004) 152-165.
Valente, Jamie S., Chemical, Structural, and Morphological Changes of a MoVTeNb catalyst . . . ACS Catal. 4, (2014) 1292-1301.
Sanfiz, A. Celaya, Preparation of Phase-Pure M1 MoVTeNb Oxide . . . Top. Catal. 50, (2008) 9-32.
Ushikubo, Takashi Ammoxidation of propane over Mo—V—Nb—Te mixed oxide catalysts, Studies in Surface Science and Catalysis 112 (1997) 473-480.
P. Botella, Solid State Science 7.
Watanabe (Applied Catal. A General, 194-195 (2000) 479-485.
Brunauer, P.H., J. Am. Chem. Soc. 60, 309 (1938).
Ivars et al., Selective oxidation of short-chain alkanes over hydrothermally prepared MoVTeNbO catalysts, Topics in Catalysis, vol. 38, Nos. 1-3, pp. 59-67, published Jul. 2006.†
Ren, et al. Enhanced Reducibility of Mg-Doped MoVTeNbOx Mixed Oxide Catalysts for Propane Oxidation Reaction, Malaysian Journal of Analytical Sciences, vol. 20, No. 6, pp. 1299-1310, published in 2016.†

\* cited by examiner
† cited by third party

Figure 1: X-ray diffraction pattern of example 1
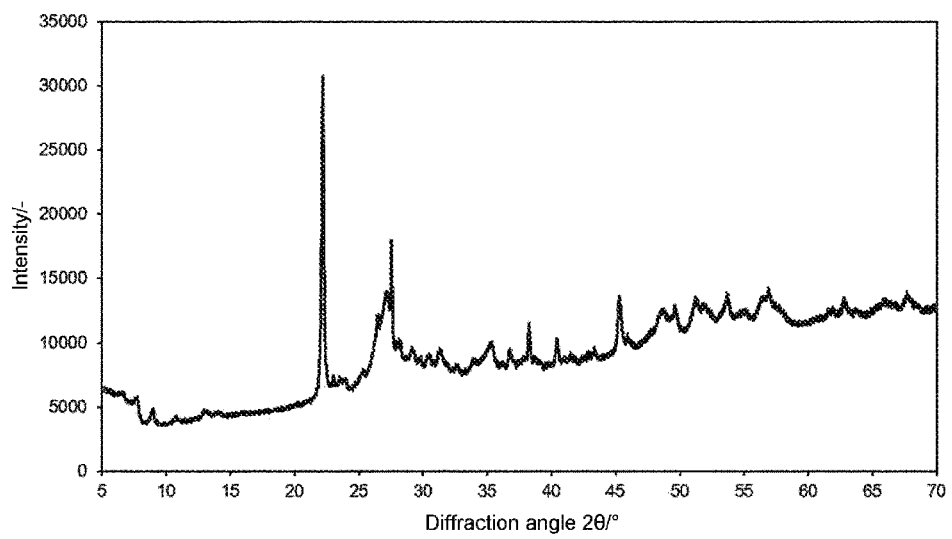

Figure 2: X-ray diffraction pattern of comparative example 1
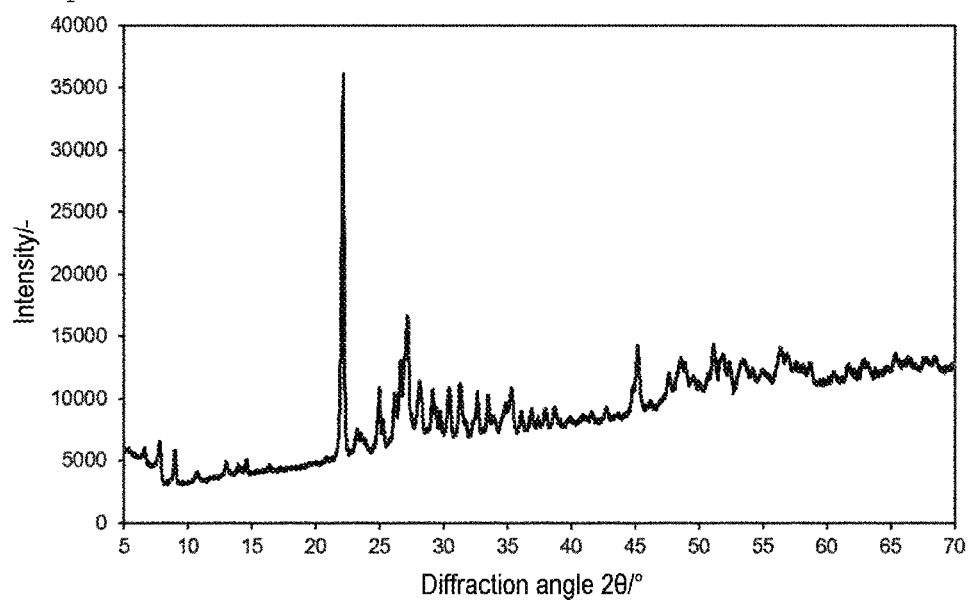

Figure 3: X-ray diffraction pattern of comparative example 2
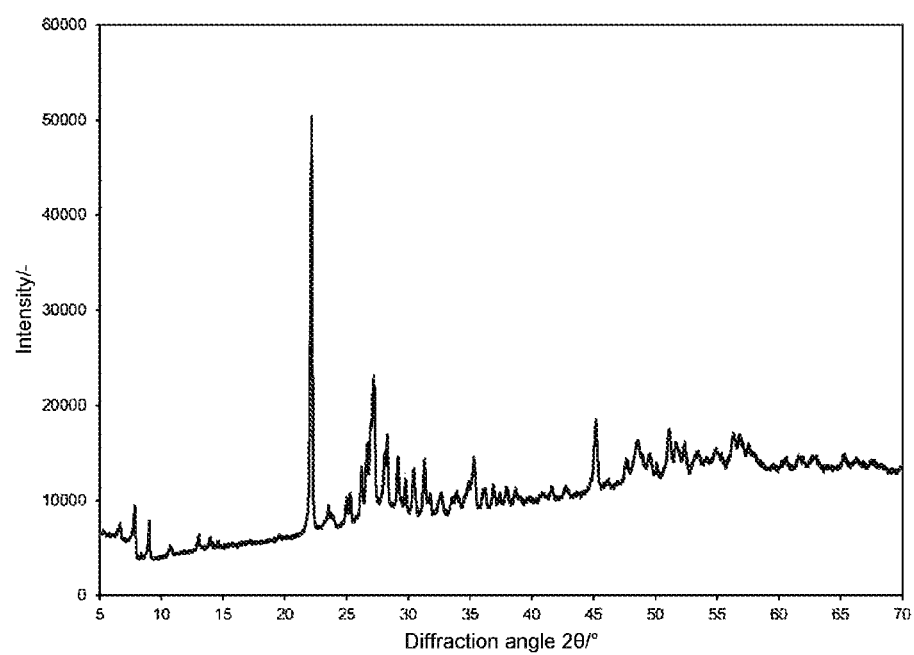

Figure 4: X-ray diffraction pattern of comparative example 2 prior to activation
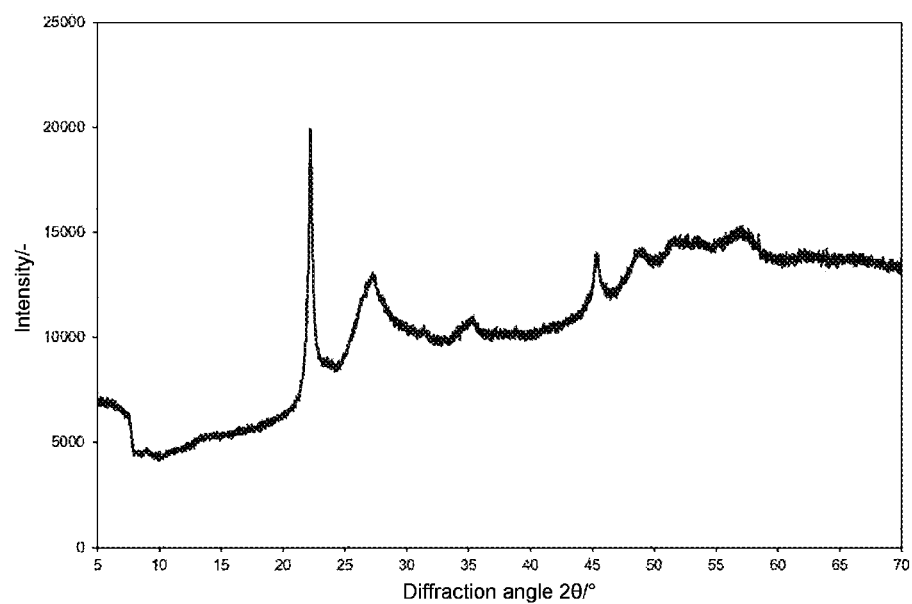

Figure 5: Pore distribution of example 1
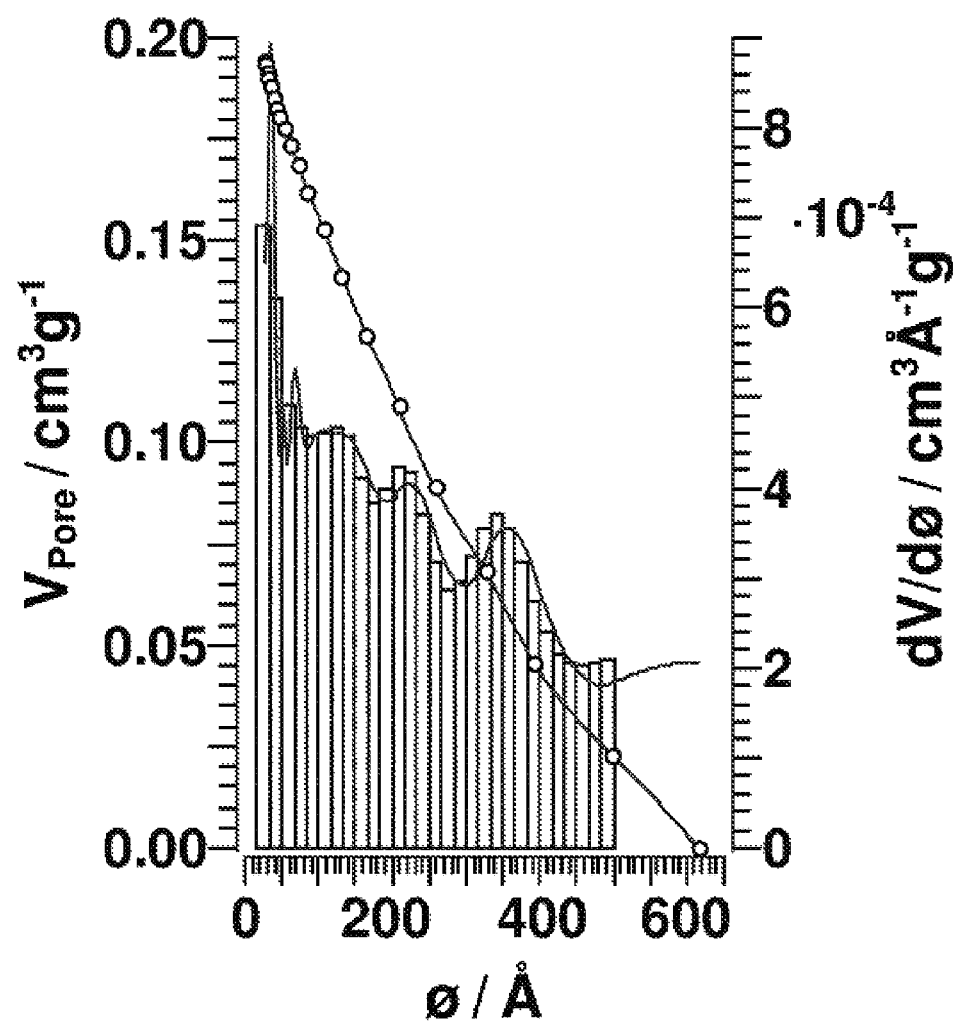

Figure 6: Pore distribution of comparative example 1
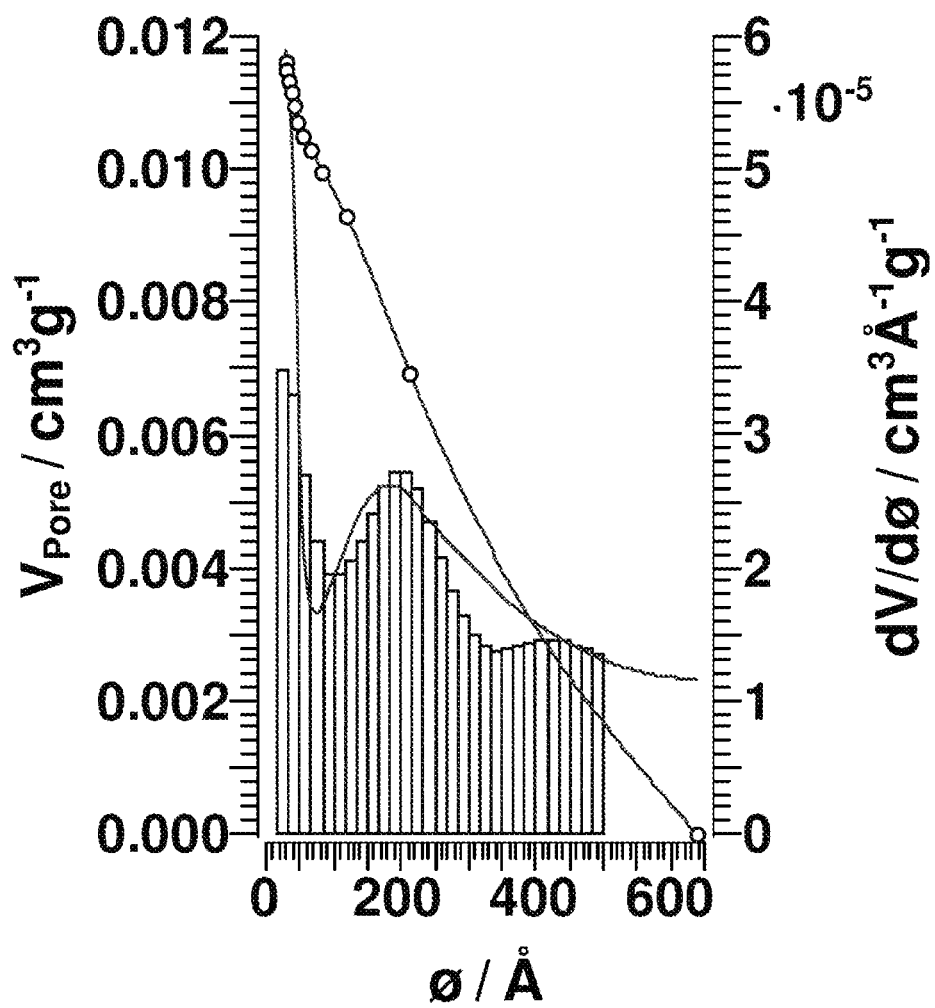

Figure 7: Pore distribution of comparative example 2
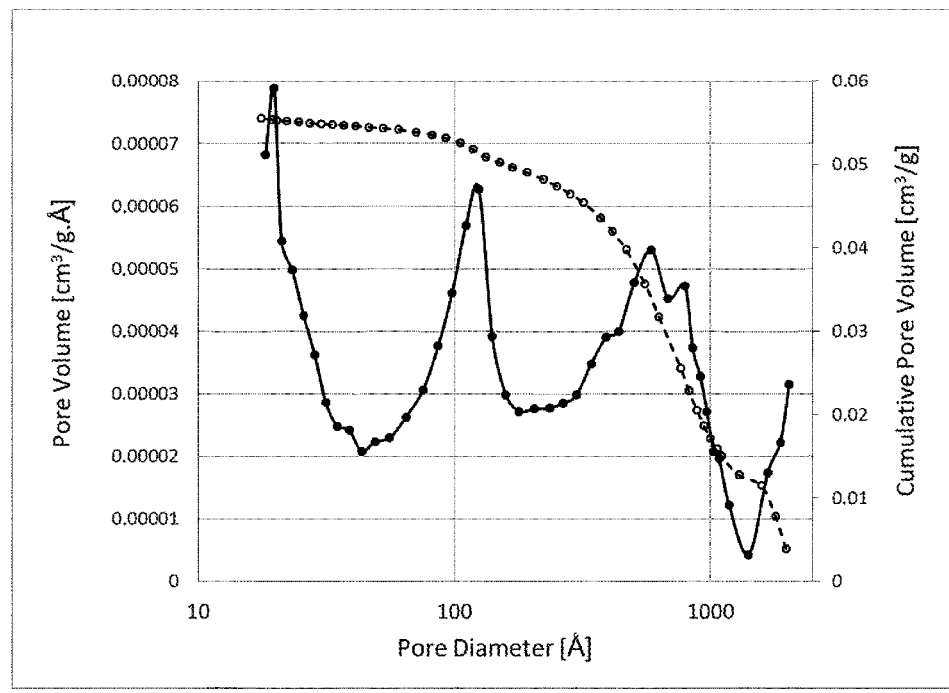

Figure 8: Activity of the catalysts in the ODH reaction of ethane
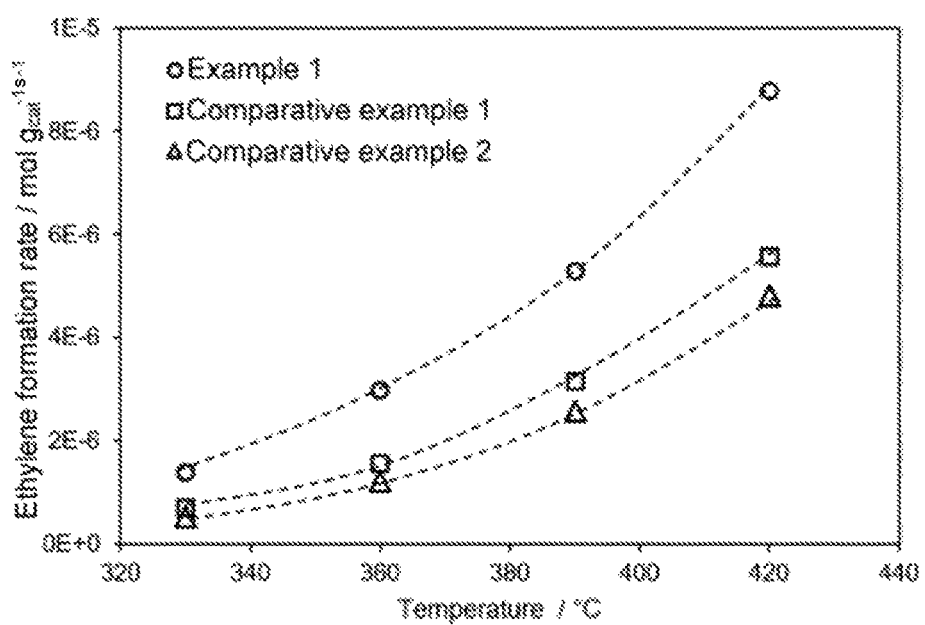

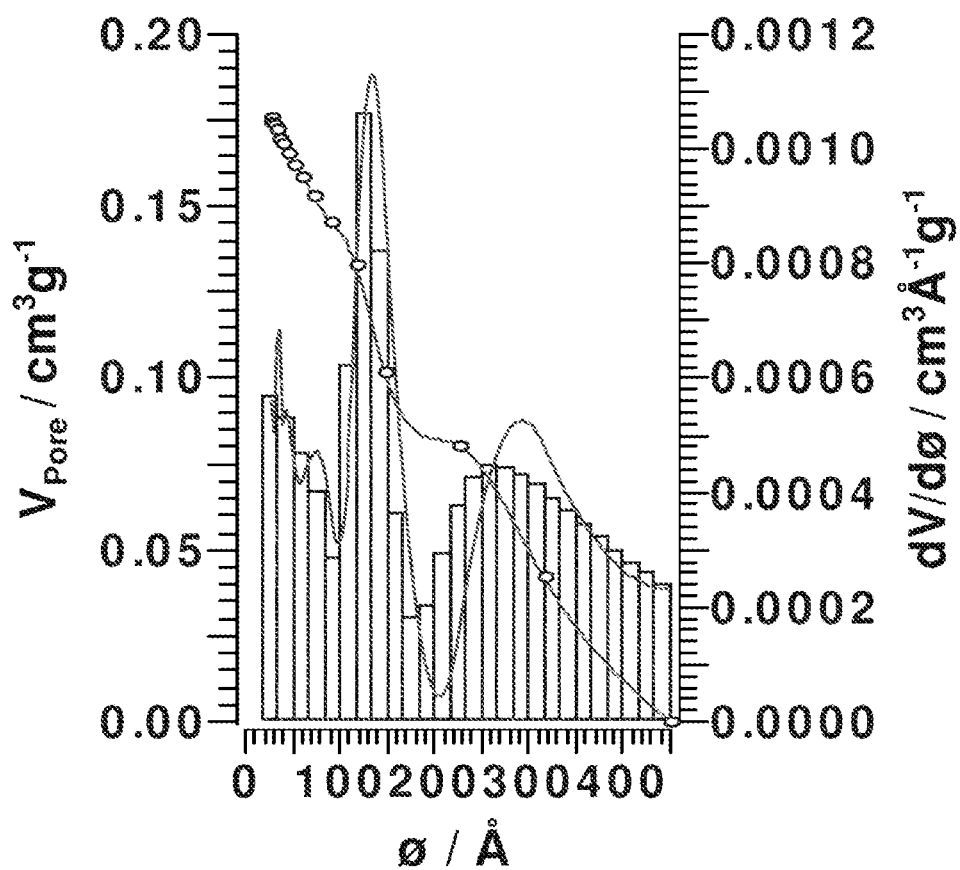
Figure 9: Pore distribution of example 2

Figure 10: Activity of the catalyst from example 2 in the ODH reaction
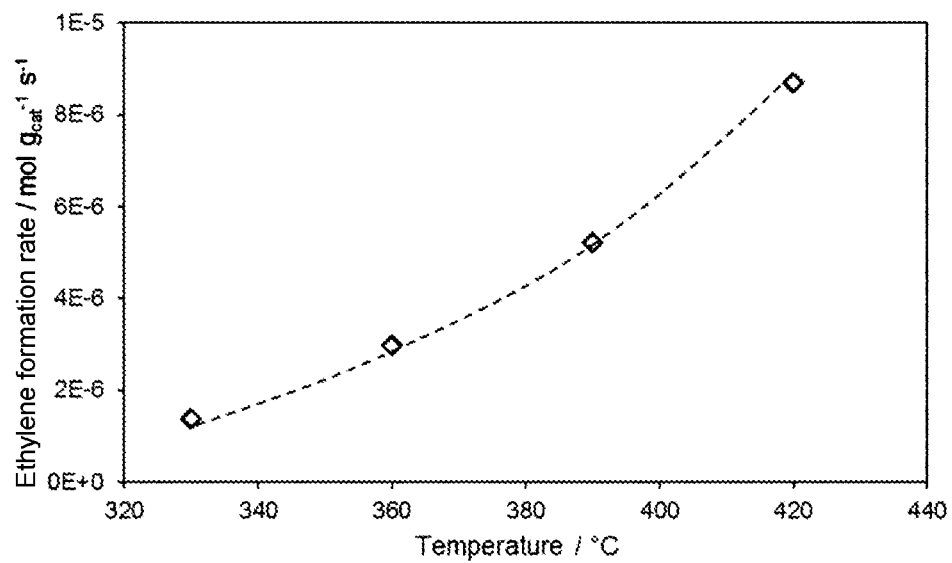

SYNTHESIS OF A MOVNBTE CATALYST HAVING AN INCREASED SPECIFIC SURFACE AND HIGHER ACTIVITY FOR THE OXIDATIVE DEHYDROGENATION OF ETHANE TO ETHYLENE

The invention relates to a novel mixed oxide material which contains molybdenum, vanadium, tellurium and niobium and the use of the mixed oxide material as catalyst for the oxidative dehydrogenation of ethane to ethene or the oxidation of propane to acrylic acid and a process for producing the mixed oxide material.

MoVNbTe mixed oxides for the oxidation of propane to acrylic acid or for the oxidative dehydrogenation of ethane to ethene are prior art. More than 200 patents and numerous scientific publications are concerned with catalysts based on MoVNbTe mixed oxides. The promotion of these mixed oxides with other metals of the Periodic Table is known. Here, the highest previously described acrylic acid yields are 60% and those of ethene are about 80%.

The MoVNbTe basis system based on four elements for a catalyst was first proposed by Mitsubishi for the ammoxidation of propane to acrylonitrile (1989, EP 318295 A2) and the oxidation to acrylic acid (1994, EP 608838 A2). JP H07-053414 (Mitsubishi) discloses a catalytic process for preparing ethylene by oxidative hydrogenation of ethane at low temperature, in high yield and with high selectivity. This process for preparing ethylene comprises contacting ethane with a gas containing molecular oxygen in the presence of a catalyst composition at elevated temperature, where the catalyst composition contains a mixed metal oxide which has molybdenum, vanadium, tellurium and oxygen as main components and displays an X-ray powder diffraction pattern which has essentially the following relative peak intensities: 2θ (+−0.4°, rel. int.: 22.1° (100), 28.2° (400~3), 36.2° (80~3), 45.1° (40~3), 50° (50~3).

MoVNbTe catalysts consist mainly of two orthorhombic phases which are referred to as "M1" and "M2" (T. Ushikubo, K. Oshima, A. Kayou, M. Hatano, Studies in Surface Science and Catalysis 112, (1997), 473). The M1 phase appears to play the important role in the selective oxidation reactions.

According to P. De Santo et al., Z. Kristallogr. 219 (2004) 152, the main phases M1 and M2 in MoVNbTe mixed oxides for selective oxidation can be described, for example, by the following structural formulae:

M1:

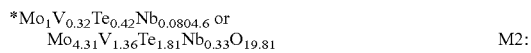

M2:

The two main phases can also occur with a somewhat different stoichiometry. Both vanadium and molybdenum are present in the center of an octahedron of oxygen atoms and are therefore partly exchangeable in the structure, so that the same structure, e.g. the M1 phase, is also possible with a higher vanadium content. A detailed study of these relationships may be found in P. Botella et al., Solid State Science 7 (2005) 507-519. The M2 phase in particular is not active for the oxidative dehydrogenation of ethane. (See J. S. Valente et al., ACS Catal. 4(2014), 1292-1301, especially p. 1293). A catalyst consisting of a very pure M1 phase is therefore desirable for the oxidative dehydrogenation of ethane. Attempts are therefore also made to produce these crystal phases cleanly and separately.

EP 529853 A2 discloses a catalyst which is suitable for preparing a nitrile from an alkane, wherein the catalyst has the empirical formula $MoV_bTe_cX_xO_n$, where X is at least one of Nb, Ta, W, Ti, Al, Zr, Cr, Mn, Fe, Ru, Co, Rh, Ni, Pd, Pt, Sb, Bi, B and Ce, b is from 0.01 to 1.0, c is from 0.01 to 1.0; x is from 0.01 to 1.0 and n is a number by means of which the total valence of the metallic elements is satisfied and the catalyst has X-ray diffraction peaks at the following 2θ angles in its X-ray diffraction pattern: diffraction angle at 2θ (22.1°+/−0.3°, 28.2°+/−0.3°, 36.2°+/−0.3°, 45.2°+/−0.3°, 50.0°+/−0.3°).

JP H07-232071 discloses a catalytic process for preparing a nitrile at a relatively low temperature and in a high yield, using an alkane as raw material and a particular catalyst. The main component of the catalyst is a mixed metal oxide composed of molybdenum, vanadium, tellurium, oxygen and X (X is one or more elements selected from the group consisting of niobium, tantalum, etc.), where the ratio of the main components, i.e. with the exception of oxygen, is expressed by the formulae I to IV: I) 0.25<rMo<0.98, II) 0.003<rV<0.50, III) 0.003<rTe<0.50, IV) 0≤rX<0.5, (rMo, rV, rTe and rX are in each case the molar parts of molybdenum, vanadium, tellurium and X) and in the XRD displays XRD bands of this mixed oxide at the various 2θ angles 9.0°±0.3°, 22.1°±0.3°, 27.3±0.3°, 29.2°±0.3° and 35.4°±0.3°. According to this document, a nitrile can be prepared in high yield at a low temperature by reacting an alkane without the presence of a halogenated substance, e.g. with water, etc., in the reaction system.

Other successful attempts to produce a pure M1 phase are based on dissolving the M2 phase out from the phase mixture. These experiments are described, for example, in EP 1301457 A2, EP 1558569 A1 or WO 2009106474 A2.

A. C. Sanfiz et al., Top. Catal. 50 (2008) 19-32, describe hydrothermal syntheses of MoVNbTe oxide. These syntheses start out exclusively from soluble compounds. Telluric acid $Te(OH)_6$ is generally used as soluble compound of tellurium. In the most readily available oxidic tellurium compound $TeO_2$, tellurium has the oxidation state +4. Unfortunately, tellurium dioxide ($TeO_2$) is sparingly soluble in water. Furthermore, the tellurium in telluric acid has the oxidation state +6. Tellurium therefore has to be oxidized up in the preparation of telluric acid. The most widespread synthesis is carried out by oxidation of tellurium oxide with hydrogen peroxide, which on a large scale is accompanied by safety problems because hydrogen peroxide can disproportionate into water and oxygen in a spontaneous decomposition. For this reason, telluric acid can be prepared in large amounts only with difficulty.

The Nb component used in the synthesis of MoVNbTe mixed oxides is generally ammonium niobium oxalate. Niobium oxide, on the other hand, is sparingly soluble and therefore has only limited suitability as starting compound.

Watanabe (Applied Catal. A General, 194-195 (2000) 479-485) describes, inter alia, the hydrothermal synthesis from the sparingly soluble precursors $MoO_3$, $V_2O_5$ and $TeO_2$. The hydrothermal synthesis gives a precursor for an ammoxidation catalyst which compared to a catalyst produced by the known dry method has twice the activity after calcination. The mixed oxides produced by a solid-state reaction display a rather low activity. It has been proposed that the higher activity of the catalyst produced by the hydrothermal synthesis is due first and foremost to the higher surface area.

A synthesis of MoVNbTe mixed oxide without use of telluric acid thus has the potential to be much less costly.

WO 2005120702 A1 describes a process for the hydrothermal production of multimetal compositions consisting of Mo and V, essentially with exclusive use of starting materials from the group of oxides, oxide hydrates, oxy acids and hydroxides for the element constituents of the oxidic multimetal compositions, where part of the element constituents present in the starting materials has an oxidation number below the maximum oxidation number.

WO 2013021034 A1 relates to a catalyst material for the oxidation and/or oxidative dehydrogenation of hydrocarbons, in particular for the selective oxidation of propane to acrylic acid, comprising a) molybdenum (Mo), b) vanadium (V), c) niobium (Nb), d) tellurium (Te), e) manganese (Mn) and cobalt, in which the molar ratio of at least one element selected from among manganese and cobalt to molybdenum is in the range from 0.01 to 0.2, more preferably from 0.02 to 0.15 and particularly preferably from 0.03:1 to 0.1:1. Furthermore, a catalyst for the oxidation and/or oxidative dehydrogenation of hydrocarbons, use of the catalyst material or of the catalyst, a process for producing a catalyst material for the oxidation and/or oxidative dehydrogenation of hydrocarbons and a process for the selective oxidation of propane to acrylic acid are indicated.

WO 2008068332 A1 relates to new mesoporous mixed metal oxide catalysts and a process for the production thereof and also the use thereof as catalyst for the oxidation of hydrocarbons or partially oxidized hydrocarbons. In particular, the disclosure relates to mesoporous mixed oxide catalysts which contain at least two, preferably at least three, different metal species, where at least one of these belongs to the group of the transition metals, to a process for producing such a catalyst, comprising a production step via the "neutral template" route and a calcination step in a substantially oxygen-free atmosphere at a temperature in the range from 300 to 700° C., to the use of such catalysts as oxidation catalysts for the preparation of oxidized hydrocarbons and in particular for the selective oxidation or ammoxidation of propane to acrylic acid and acrylonitrile. A preferred catalyst comprises the elements Mo, V, Te and Nb.

In all the syntheses of the M1 phase described in the prior art, the M1 phase is only formed in a high-temperature treatment, typically above 500° C., under inert gas after the reaction of the starting materials ("activation"). In the present invention, a synthesis method for preparing a highly pure M1 phase which dispenses with the concluding high-temperature treatment has been found.

It was therefore an object of the present invention to find a mixed oxide material containing molybdenum, vanadium, tellurium and niobium ("MoVTeNb mixed oxide") which has the M1 phase and a maximum specific surface area. It was a further object of the invention to find a MoVTeNb mixed oxide that has maximum activity as catalyst material for the oxidation of alkanes.

The object is achieved by a mixed oxide material comprising the elements molybdenum, vanadium, niobium and tellurium which in the XRD using Cu-Kα radiation has diffraction reflections h, i, k and l whose peaks are at the diffraction angles (2θ) 26.2°±0.5° (h), 27.0°±0.5° (i), 7.8°±0.5° (k) and 28.0°±0.5° (l), characterized in that the mixed oxide material has a pore volume of >0.1 cm$^3$/g.

The MoVTeNb mixed oxide of the invention is prepared by a process for producing a mixed oxide material comprising the steps:
 a) production of a mixture of starting compounds containing molybdenum, vanadium, niobium and a tellurium-containing starting compound in which tellurium is present in the oxidation state +4 and also oxalic acid and at least one further oxo ligand, b) hydrothermal treatment of the mixture of starting compounds at a temperature of from 100 to 300° C. to give a product suspension,
 c) isolation and drying of the mixed oxide material present in the suspension resulting from step b).

The starting compounds are the molybdenum-, vanadium-, tellurium- and niobium-containing starting materials of the hydrothermal synthesis (precursor compounds). These each contain one or more of the elements molybdenum, vanadium, tellurium or niobium.

The molybdenum-containing starting compound can, for example, be an ammonium heptamolybdate or molybdenum trioxide, the vanadium-containing starting compound can, for example, be an ammonium metavanadate, vanadyl sulfate or vanadium pentoxide, the niobium-containing starting compound can, for example, be ammonium niobium oxalate or niobium oxalate or niobium oxide. The tellurium-containing starting compound according to the invention is one in which tellurium is present in the oxidation state +4, i.e. as tellurium(IV) cation, for example tellurium dioxide or a compound of the formula $M_x^{n+}TeO_3$ (where n=1 or 2 and x=2/n), where M is an alkali metal or alkaline earth metal, e.g. $Na_2TeO_3$. The tellurium-containing starting compound is particularly preferably tellurium dioxide which can be present in any degree of hydration.

An advantage of the production process of the invention is that a synthesis of the M1 phase from insoluble and inexpensive oxides is possible, e.g. $MoO_3$, $V_2O_5$, $Nb_2O_5$ and $TeO_2$ and a combination of oxalic acid and at least one further oxo ligand. As further oxo ligands (i.e. in addition to oxalic acid), dicarboxylic acids and diols and also organic compounds having two adjacent carbon atoms which each bear a hydroxy group have been found to be particularly useful. Preference is given to using a mixture of citric acid and glycol as further oxo ligand.

The oxalic acid should preferably be present in the mixture of the starting compounds in an Mo/oxalic acid ratio of from 1:0.01 to 1:1, preferably from 1:0.08 to 1:0.4, more preferably from 1:0.15 to 1:0.25.

The at least one further oxo ligand, or all further oxo ligands together, should preferably be present in the mixture of the starting compounds in an Mo/oxo ligand ratio of from 1:0.01 to 1:1, preferably from 1:0.025 to 1:0.2, more preferably from 1:0.05 to 1:0.1.

The synthesis of the invention also surprisingly gives the M1 phase straight after hydrothermal synthesis and drying, without an energy-intensive high-temperature treatment at a temperature above 400° C. being necessary. Surprisingly, the amount of tellurium and niobium used can be significantly reduced when using this procedure, but the catalytically active M1 phase is nevertheless formed in high phase purity.

A further advantage of the inventive synthesis of the M1 phase is the high efficiency of the conversion of the starting materials by the hydrothermal synthesis. If the stoichiometry of the reactants varies within the range of Mo/V/Nb/Te=1: 0.22:0.1:0.1 to 1:0.3:0.17:0.17, Mo, V, Nb and Te are converted almost completely to the M1 phase, such that less than 100 ppm of all metals remain in the mother liquor.

The possible stoichiometry of the M1 phase is sufficiently well known from the literature and can be by the formula $Mo_1V_aNb_bTe_cO_x$ with a=0.2 to 0.3, b=0.1 to 0.2, c=0.1 to 0.25 and x, depending on the oxidation state of the metals (Mo, V, Nb and Te), a quantity that leads to balancing of charge.

Preferably, no ammonium ions are present during the synthesis. The preparation process of the invention permits the synthesis of a mixed MoVNbTe oxide including the M1 phase. Drying gives rise here to a mixed MoVNbTe oxide having a pore volume of more than 0.1 cm$^3$/g and a high specific surface area of more than 20 m$^2$/g and more preferably of more than 30 m$^2$/g. The mixed MoVNbTe oxide of the invention is therefore particularly suitable as catalyst material since a high pore volume and a high specific surface area is generally desirable for catalytic applications.

The mixture of starting compounds is preferably present as aqueous suspension and is subsequently hydrothermally treated. The term "hydrothermally" refers predominantly to reaction conditions for producing a catalyst material in the presence of water and at elevated temperature and/or elevated pressure, for example in an autoclave. Here, the pressure can be in the range from 5 to 30 bar, preferably from 10 to 27 bar. Illustrative pressure ranges are from 11 to 20 bar.

As a result of the hydrothermal treatment (step b)), a product suspension containing the MoVNbTe mixed oxide as solid is obtained. In the process of the invention, the isolation of the solid of the suspension, which represents the MoVNbTe mixed oxide according to the invention, in step c) can be carried out in one or more filtration steps, e.g. by filtering-off of the mother liquor. Drying can be carried out in a single step or in two steps in flowing or static air. The first drying step is preferably carried out at from 60° C. to 150° C. (particularly preferably from 80° C. to 120° C.), and a second drying step can be carried out at from 200° C. to 400° C. In addition, step c) of the process of the invention can comprise one or more washing steps, calcination steps (thermal treatment) and/or milling steps. The calcination can be carried out at from 200 to 500° C., preferably from 250° C. to 350° C., in air.

The mixed MoVNbTe oxide of the invention can be used as catalyst material for the oxidation and/or oxidative dehydrogenation ("ODH") of hydrocarbons, in particular for the oxidative dehydrogenation of ethane to ethylene.

The catalyst or the catalyst material is a mixed MoVNbTe oxide which is produced by the process of the invention and can be used in various ways in a commercial catalyst. For example, it can be processed by tableting to give catalyst pellets which can then be introduced into a reactor.

Preferably, the mixed MoVTeNb oxide which is obtained by the process of the invention is used as catalyst material without further calcination, i.e. immediately after drying.

The catalyst material can also be processed together with a suitable binder to give an extrudate (pellets, shaped bodies, honeycomb bodies and the like). As binder, it is possible to use any binder material with which a person skilled in the art is familiar and which appears suitable. Preferred binders are, inter alia, pseudoboehmite and also siliceous binders such as colloidal silicon oxide or silica sol.

The catalyst material can also be processed together with other components, preferably with a binder, particularly preferably with an organic binder, for example an organic adhesive, polymers, resins or waxes, to give a washcoat which can be applied to a metallic or ceramic support. Additional impregnation steps or calcination steps can optionally be carried out.

The MoVNbTe mixed oxide of the invention is used as catalyst material in the examples and will therefore sometimes be referred to as catalyst in the experimental part.

FIG. 1: X-ray diffraction pattern of the inventive catalyst of example 1.

FIG. 2: X-ray diffraction pattern of the comparative catalyst of comparative example 1.

FIG. 3: X-ray diffraction pattern of the comparative catalyst of comparative example 2, after activation.

FIG. 4: X-ray diffraction pattern of the comparative catalyst of comparative example 2, prior to activation.

FIG. 5: pore distribution of the catalyst of example 1.

FIG. 6: pore distribution of the catalyst of comparative example 1.

FIG. 7: pore distribution of the catalysts of comparative example 2.

FIG. 8: activity of the catalysts in the ODH reaction of ethane.

FIG. 9: pore distribution of the catalyst of example 2.

FIG. 10: activity of the catalyst of example 2 in the ODH reaction.

It can be seen that the X-ray diffractogram (XRD) of the catalyst according to the invention in FIG. 1 has the typical reflections of the M1 phase at (2θ=)26.2°±0.5° (h), 27.0°±0.5° (i), 7.8°±0.5° (k) and 28.0°±0.5° (l) (when using Cu-Kα radiation). These reflections are broader than in the comparative examples treated by activation (FIGS. 2 and 3). The greater width is explained in that the crystallite size is smaller, which is associated with the greater specific surface area. It can be seen in FIG. 4 that without the activation, only the reflection at 22.5°, which indicates the plane spacing, can be clearly identified. Only after the high-temperature treatment (FIG. 3) does this catalyst display the typical reflections of the M1 phase.

Methods of Characterization:

To determine the parameters of the catalysts according to the invention, the following methods are used:

1. BET Surface Area:

The determination is carried out by the BET method of DIN 66131; a publication of the BET method may also be found in J. Am. Chem. Soc. 60,309 (1938). The measurements were carried out at 77 K on a Sorptomatic 1990 instrument. The sample was evacuated for 2 hours at 523 K before the measurement. The linear regression of the isotherms according to the BET method was carried out in a pressure range of $p/p_0$=0.01-0.3 ($p_0$=730 torr).

2. N$_2$ Pore Distribution

The pore size distribution was conducted by means of nitrogen sorption measurements using a Sorptomatic instrument or a TriStar 3000 instrument at 77 K. Before the measurement, the sample was evacuated at 523 K for 2 h. Both adsorption and desorption isotherms were determined and used for evaluation by the Barrett-Joyner-Halenda (BJH) method.

3. X-Ray Powder Diffraction (XRD)

The X-ray diffraction pattern was produced by X-ray powder diffraction (XRD) and evaluation according to the Scherrer formula.

The diffraction patterns were recorded on a PANalytical Empyrean, equipped with a Medipix PIXcel 3D detector, in θ-θ geometry in an angle range of 2θ=5-70°. The X-ray tube produced Cu-K radiation. The Cu-Kβ radiation was suppressed by use of an Ni filter in the beam path of the incident X-ray beam, so that only Cu-Kα radiation having a wavelength of 15.4 nm (E=8.04778 keV) was diffracted by the sample. The height of the source-side beam path was adapted by means of an automatic divergence slit (programmable divergence slit—PDS) in such a way that the sample was irradiated over a length of 12 mm over the entire angle range. The width of the detector-side X-ray beam was restricted to 10 mm by means of a fixed orifice plate. Horizontal divergence was minimized by use of a 0.4 rad Soller slit.

The height of the detector-side beam path was adapted in a manner analogous to the source-side beam path by means of an automatic anti-scatter slit (programmable anti-scatter slit—PASS) in such a way that the X-ray beam reflected by the sample over a length of 12 mm was detected over the entire angle range.

The samples, depending on the amount available, were prepared either on an amorphous silicon sample plate or tableted as flat-bed samples.

WORKING EXAMPLES

Example 1

75 ml of twice-distilled water were placed in a 100 ml PTFE beaker, 177.8 mg of monoethylene glycol were added dropwise and 5397.9 mg of $MoO_3$, 1023.9 mg of $V_2O_5$, 599.1 mg of $TeO_2$, 549.5 mg of $Nb_2O_5.xH_2O$ (Nb=63.45% by weight), 540.9 mg of citric acid and 338.3 mg of oxalic acid were subsequently slurried in. The Teflon beaker was closed and transferred into a stainless steel autoclave bomb. This was closed in a pressure-tight manner and clamped onto a horizontal rotating shaft in an oven which had been preheated to 190° C. After 48 hours, the autoclave bomb was taken from the oven and immediately quenched under running water and subsequently cooled in an ice bath for 45 minutes.

The product suspension formed was filtered through a filter paper (pore width 3 μm) and the solid was washed with 200 ml of twice-distilled water.

The product obtained in this way was dried at 80° C. for 16 h in a drying oven and then ground in a hand mortar.

A yield of solid of 6.2 g was achieved. The BET surface area of the product was 83.3 m$^2$/g, and the product had a pore volume of 0.2 cm$^3$/g and a pore distribution shown in FIG. 5.

Example 2

The synthesis was conducted as described in example 1, except that, after drying at 80° C. for 16 h, there was a further drying step at 400° C. for 3 h. The BET surface area of the product was 59.0 m$^2$/g; the product had a pore volume of 0.176 cm$^3$/g and a pore distribution which is shown in FIG. 9.

It can be seen from FIG. 10 that, at 420° C., the catalyst, with an ethylene formation rate of $9 \times 10^{-6}$ mol g$^{-1}_{cat}$ s$^{-1}$, had about the same activity as the catalyst from example 1 that had merely been dried at 80° C. (FIG. 8). The loss of activity thus does not occur until within the temperature range above 400° C.

Comparative Example 1

The catalyst described in example 1 was subjected to a heat treatment (activation) in a tube furnace. For this purpose, 1 g of the dried solid was transferred to a porcelain boat so that the bottom of the boat is covered with powder to a height of about 2 mm.

Activation was carried out at 600° C. for 2 hours (heating rate: 10° C./min; $N_2$: 100 ml/min). After this treatment the BET surface area was 7.3 m$^2$/g, and the product had a pore volume of 0.013 cm$^3$/g and a pore distribution shown in FIG. 6.

Comparative Example 2

3.3 l of distilled $H_2O$ were placed in an autoclave (40 l) and heated to 80° C. while stirring. Meanwhile, 725.58 g of ammonium heptamolybdate tetrahydrate (from HC Starck) was introduced and dissolved (AHM solution). In each of three 5 l glass beakers, 1.65 l of distilled $H_2O$ was likewise heated to 80° C. while stirring on a magnetic stirrer with temperature regulation. 405.10 g of vanadyl sulfate hydrate (from GfE, V content: 21.2%), 185.59 g of ammonium niobium oxalate (HC Starck, Nb content: 20.6%) and 94.14 g of telluric acid (V solution, Nb solution and Te solution), respectively, were then introduced into these glass beakers and dissolved.

The V solution, then the Te solution and finally the Nb solution were then pumped by means of a peristaltic pump into the AHM solution (pumping time: V solution: 4.5 min at 190 rpm, tube diameter: 8×5 mm, Nb solution: 6 min at 130 rpm, tube diameter: 8×5 mm).

The suspension formed was now stirred further at 80° C. for 10 minutes. The speed of the stirrer during the precipitation was 90 rpm.

The suspension was subsequently blanketed with nitrogen by building up a pressure up to about 6 bar in the autoclave by means of nitrogen and opening the discharge valve to such an extent that flow under a pressure of $N_2$ occurs through the autoclave (5 minutes). At the end, the pressure was released again to a residual pressure of 1 bar via the venting valve.

The hydrothermal synthesis was carried out at 175° C. for 20 hours (heating time: 3 hours) in the 40 l autoclave using an anchor stirrer at a stirrer speed of 90 rpm.

After the synthesis, the suspension was filtered on a blueband filter by means of a vacuum pump and the filter cake was washed with 5 l of distilled $H_2O$.

Drying was carried out at 80° C. for 3 days in a drying oven and the solid was subsequently milled in an impact mill, giving a yield of solid of 0.8 kg.

The calcination was carried out at 280° C. for 4 hours (heating rate 5° C./min, air: 1 l/min).

Activation was carried out in an $N_2$ flow in a retort at 600° C. for 2 hours (heating rate 5° C./min, $N_2$: 0.5 l/min).

The product had a BET surface area of 13 m$^2$/g and a pore volume of 0.055 cm$^3$/g with a pore distribution shown in FIG. 7.

Comparative Example 3

The catalyst from comparative example 1 was used immediately after the calcination at 280° C. for 4 hours. The calcination at 600° C. under nitrogen for 2 hours was not carried out.

Example 3

The catalytic activity of the catalysts of example 1 and comparative examples 1 and 2 in the oxidative dehydrogenation ("ODH") of ethane was examined in the temperature range from 330° C. to 420° C. at atmospheric pressure in a tube reactor. For this purpose, 25 mg (example 1 and comparative example 1) or 200 mg (comparative example 2) of catalyst (particle size 150-212 μm) were in each case diluted with silicon carbide (particle size from 150 to 212 μm) in a mass ratio of 1:5. A layer of 250 mg of silicon carbide of the same particle size was introduced both below and above the catalyst bed and the ends of the tube reactor were closed by means of silica wool plugs.

The reactor was flushed with inert gas before commencement of the experiment and subsequently heated to 330° C. under a helium flow of 50 sccm. After the desired temperature had been reached and was stable for 1 hour, the gas fed in was switched over to the reaction gas mixture.

The inlet gas composition was $C_2H_6/O_2/He=9.1/9.1/81.8$ (v/v) at a total volume flow of 50 sccm.

Analysis of the product gas stream was carried out in a gas chromatograph equipped with Haysep N and Haysep Q columns, a 5 A molecular sieve column and a thermal conductivity detector.

The ethylene formation rates under the above-described conditions are shown in FIG. 8.

The catalyst activity was normalized to the catalyst mass; the catalyst according to the prior art made from the soluble precursor compounds (comparative example 2) shows the lowest activity. Comparative example 1 has been prepared by the novel process of this patent, but was still calcined at 600° C. The highest catalytic activity is shown by the inventive catalysts without final high-temperature treatment.

TABLE 1

|  | BET [m²/g] | Pore volume [cm³/g] |
|---|---|---|
| Example 1 | 83.3 | 0.2 |
| Example 2 | 59.0 | 0.176 |
| Comparative example 1 | 7.3 | 0.013 |
| Comparative example 2 | 13 | 0.055 |
| Comparative example 3 | (69) almost amorphous |  |

Table 1 compares the BET surface areas and the pore volume of the catalyst according to the invention together with comparative examples.

The invention claimed is:

1. A mixed oxide material comprising the elements molybdenum, vanadium, niobium and tellurium which in the XRD using Cu-Kα radiation has diffraction reflections h, i, k and l whose peaks are approximately at the diffraction angles (2θ) 26.2°±0.5° (h), 27.0°±0.5° (i), 7.8°±0.5° (k) and 28.0°±0.5° (l), wherein the mixed oxide material has a pore volume of greater than 0.1 cm³/g.

2. The mixed oxide material as claimed in claim 1, wherein it has a BET surface area of more than 30 m²/g.

3. The mixed oxide material as claimed in claim 1, wherein it has a volume of the pores smaller than 10 nm of more than 0.2 cm³/g.

4. The mixed oxide material as claimed in claim 1, wherein the molar Mo:Te ratio is ≤11 and the molar Mo:Nb ratio is ≤11.

5. The mixed oxide material as claimed in claim 1, including an M1 crystalline phase having the formula

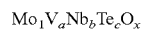

wherein a is 0.2-0.3, b is 0.1-0.2, c is 0.1-0.25, and x is selected such that the overall charge of the empirical formula is zero.

6. The mixed oxide material as claimed in claim 5, wherein it has a BET surface area of more than 30 m²/g.

7. The mixed oxide material as claimed in claim 5, wherein it has a volume of the pores smaller than 10 nm of more than 0.2 cm³/g.

* * * * *